(12) United States Patent
Gilkey et al.

(10) Patent No.: US 11,766,309 B2
(45) Date of Patent: Sep. 26, 2023

(54) ARTICLES, KITS AND METHODS ADAPTED FOR FACILITATING ADJUSTABILITY OF OPERATIVE APPARATUSES

(71) Applicant: ClearCam Inc., Austin, TX (US)

(72) Inventors: Mitchell Ross Gilkey, Austin, TX (US); Alexander Ross Cohen, Austin, TX (US)

(73) Assignee: ClearCam Inc., Austin, TX (US)

( * ) Notice: Subject to any disclaimer, the term of this patent is extended or adjusted under 35 U.S.C. 154(b) by 427 days.

(21) Appl. No.: 17/195,704

(22) Filed: Mar. 9, 2021

(65) Prior Publication Data

US 2022/0287796 A1 Sep. 15, 2022

(51) Int. Cl.
- *A61B 1/00* (2006.01)
- *A61B 90/70* (2016.01)
- *A61B 50/30* (2016.01)

(52) U.S. Cl.
CPC .............. *A61B 90/70* (2016.02); *A61B 50/30* (2016.02); *A61B 2090/701* (2016.02); *A61B 2560/0487* (2013.01)

(58) Field of Classification Search
CPC ... A61B 90/70; A61B 50/30; A61B 2090/701; A61B 2560/0487; A61B 1/126;
(Continued)

(56) References Cited

U.S. PATENT DOCUMENTS

| | | | |
|---|---|---|---|
| 5,392,766 A | 2/1995 | Masterson et al. | |
| 5,415,656 A | * 5/1995 | Tihon | A61B 18/14 606/46 |

(Continued)

FOREIGN PATENT DOCUMENTS

| | | |
|---|---|---|
| CN | 101883531 B | 7/2014 |
| EP | 0647425 A1 | 4/1995 |

(Continued)

OTHER PUBLICATIONS

Advanced Packaging Inc. (webpage, "Medical Industry Solutions", https://web.archive.org/web/20201125172326/https://advpack.com/industry/medical/ , Nov. 25, 2020) (Year: 2020).*

(Continued)

*Primary Examiner* — Timothy J Neal
*Assistant Examiner* — James Edward Boice
(74) *Attorney, Agent, or Firm* — David O. Simmons; IVC Patent Agency

(57) ABSTRACT

Embodiments of the disclosures made herein are directed to facilitating adjustability of operative apparatuses. More specifically, embodiments of the disclosures made herein are directed to mitigating adverse implications of having to adjust a control portion of an operative apparatus to a user-defined setting that is not otherwise a predefined setting position of the control portion. Such adverse implications may arise, for example, due to the time required for performing such adjustment with a required degree of precision. Thereby, such embodiments serve to mitigate, if not eliminate, that manner in which adjusting the control portion of the operative apparatus to the user-defined setting during a procedure can undesirably and/or unacceptably limit efficiency and/or effectiveness of the procedure.

7 Claims, 4 Drawing Sheets

(58) Field of Classification Search
CPC ...... A61B 2018/0097; A61B 2562/245; A61B 1/0008; A61B 1/00131; A61B 1/00135; A61B 1/00142; A61B 50/00
USPC ..... 600/133, 109, 157, 169, 121, 127; 422/1
See application file for complete search history.

(56) References Cited

U.S. PATENT DOCUMENTS

| | | | |
|---|---|---|---|
| 5,518,502 A | | 5/1996 | Kaplan et al. |
| 6,755,782 B2 | | 6/2004 | Ogawa |
| 6,923,759 B2 | | 8/2005 | Kasahara et al. |
| 7,543,314 B2 | | 6/2009 | Kadykowski |
| 7,959,561 B2 | | 6/2011 | Akui et al. |
| 8,690,764 B2 | | 4/2014 | Clark et al. |
| 8,979,738 B2 | | 3/2015 | Hsu et al. |
| 9,050,036 B2 | | 6/2015 | Poll et al. |
| 9,486,129 B2 | | 11/2016 | Rodriguez Sanjuan |
| 9,763,567 B2 | | 9/2017 | O'Prey et al. |
| 10,791,918 B1 | | 10/2020 | Gilkey et al. |
| 2005/0000553 A1* | 1/2005 | Noguchi | A61B 1/125 134/84 |
| 2009/0229067 A1 | | 9/2009 | Becker et al. |
| 2009/0250081 A1 | | 10/2009 | Gordin et al. |
| 2012/0101338 A1 | | 4/2012 | O'Prey et al. |
| 2013/0217970 A1* | 8/2013 | Weisenburgh, II | A61B 1/126 600/157 |
| 2014/0094650 A1 | | 4/2014 | Schaning |
| 2014/0346068 A1* | 11/2014 | Omura | B65D 25/06 206/534 |
| 2016/0038001 A1* | 2/2016 | Perez-Lizano | A61B 1/05 128/200.26 |
| 2016/0128551 A1 | | 5/2016 | Hsu et al. |
| 2017/0332893 A1 | | 11/2017 | Irion et al. |
| 2017/0367571 A1 | | 12/2017 | Nave |

FOREIGN PATENT DOCUMENTS

| | | |
|---|---|---|
| JP | S5861723 A | 4/1983 |
| JP | H01204637 A | 8/1989 |
| JP | 04-362912 | 12/1992 |
| JP | H05103748 A | 4/1993 |
| JP | 2015031026 A | 2/2015 |
| JP | 5735908 B2 | 6/2015 |
| WO | 200912587 A2 | 10/2009 |
| WO | 2014034839 A1 | 3/2014 |
| WO | WO2017006684 | 12/2017 |
| WO | 2020112852 A1 | 4/2020 |

OTHER PUBLICATIONS

International Search Authority, Notification of Transmittal of the International Search Report and Written Opinion of the International Search Authority, PCT/US2019/063369, 16 pages.

* cited by examiner

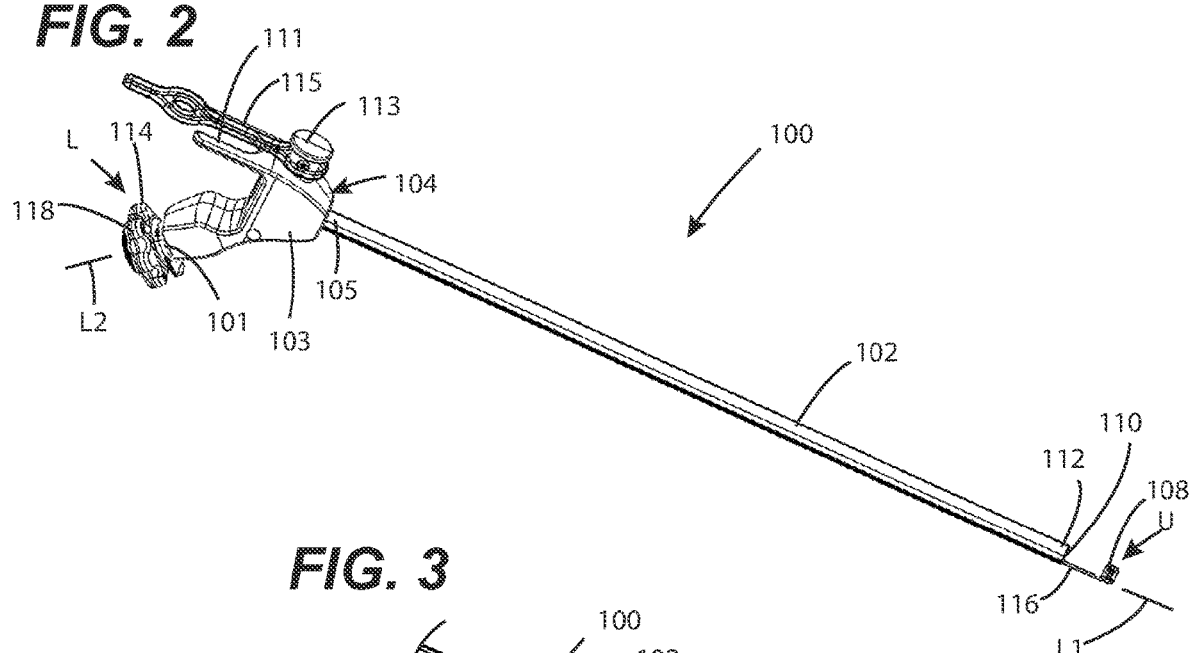
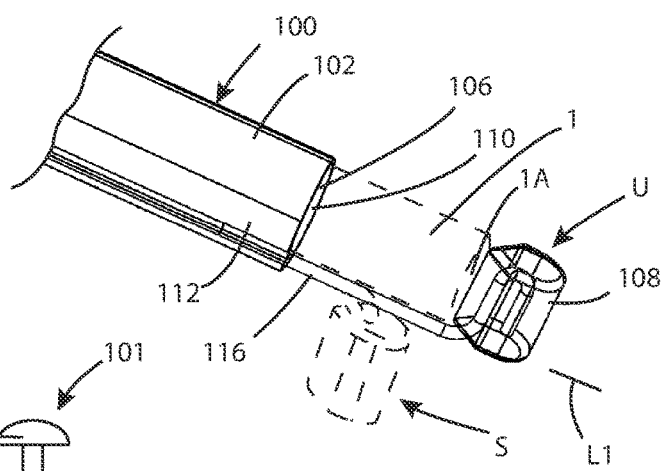
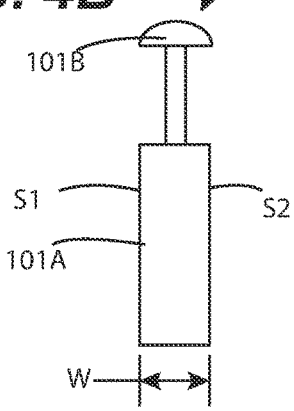
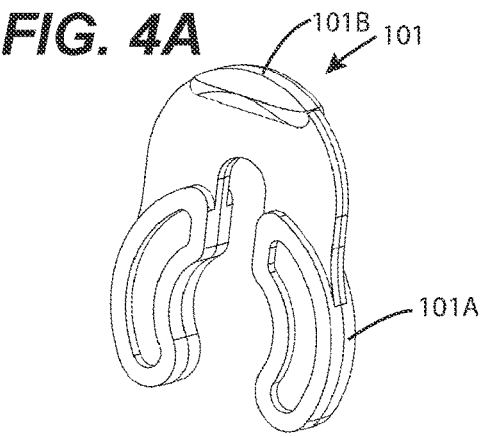

ARTICLES, KITS AND METHODS ADAPTED FOR FACILITATING ADJUSTABILITY OF OPERATIVE APPARATUSES

FIELD OF THE DISCLOSURE

The disclosures made herein relate generally to operative apparatuses and, more particularly, such disclosures are related to articles, kits and methods adapted for facilitating adjustability of operative apparatuses.

BACKGROUND

Operative apparatuses (e.g., instruments) are known to be used in a variety of industries and applications. Such operative apparatuses are used in performing one or more tasks of a procedure—e.g., a surgical procedure, a medical procedure, a manufacturing procedure and the like. The tasks may be performed via manual control of such operative apparatuses, system-automated control of such apparatuses or the like. To this end, such operative apparatuses generally have a control portion coupled to an effector portion, whereby input to the control portion causes one or more responsive actions at the effector portion.

It is known that the control portion of operative apparatuses often requires adjustment during a given procedure to alter an operative aspect of the effector portion. In some cases, the adjustment is between two or more predefined setting position of the operative apparatus. However, in some other cases, the adjustment involves setting an operative apparatus at a user-defined setting that is not a predefined setting position of the operative apparatus—e.g., not visually, mechanically, electronically or otherwise denoted. Thus, such adjustment may be solely dictated by a user of the operative apparatus manually positioning the control portion of the operative apparatus. Where a procedure involves a plurality of instances of having to set the operative apparatus at such a user-defined setting, manual adjustment to the user-defined setting can undesirably and/or unacceptably limit efficiency and/or effectiveness of the procedure—e.g., due to the time required for performing such adjustment with a required degree of precision.

Therefore, an effective, efficient, simple and reliable approach for mitigating the adverse implications of having to manually adjust the operative apparatus to a user-defined setting that is not a predefined setting position of the operative apparatus would be advantageous, desirable and useful.

SUMMARY OF THE DISCLOSURE

Embodiments of the disclosures made herein are directed to facilitating adjustability of operative apparatuses. More specifically, embodiments of the disclosures made herein are directed to mitigating adverse implications of having to manually adjust a control portion of an operative apparatus to a user-defined setting that is not otherwise a predefined setting position of the operative apparatus. An imaging element cleaning apparatus used with a visualization scope (e.g., laparoscope) is an example of such an operative apparatus. The aforementioned adverse implications may arise, for example, due to the time required for performing such manual adjustment with a required degree of precision. Thereby, such embodiments serve to mitigate, if not eliminate, the manner in which manually adjusting the control portion of the operative apparatus to the user-defined setting during a procedure can undesirably and/or unacceptably limit efficiency and/or effectiveness of the procedure.

In one or more embodiments of the disclosures made herein, an imaging element cleaning apparatus adapted for use with a visualization scope comprises a user interface body, a control body and at least one spacer body. The control body includes a force input (e.g., hand-gripping) portion and a mounting member. The mounting member has a first end portion attached to the force input portion and a second end portion translatably attached to the user interface body to thereby enable an overall amount of axial displacement of the mounting member (e.g., the first end portion thereof) relative to the user interface body along an axial reference axis. The at least one spacer body is located between the control body and the user interface body to limit axial translation of the control body and thereby provide a spacer-limited amount of axial displacement of the mounting member relative to the user interface body that is less that the overall amount of axial displacement by an amount defined by the width of each spacer body attached to the control body.

In one or more embodiments of the disclosures made herein, a kit comprises an imaging element cleaning apparatus and a plurality of spacer bodies. The imaging element cleaning apparatus includes a user interface body and a control body. The control body includes a force input (e.g., hand-gripping) portion and a mounting member. A first end portion of the mounting member is attached to the force input portion. A second end portion of the mounting member is translatably attached to the user interface body to thereby enable axial displacement of the first end portion of the mounting member relative to the user interface body along an axial reference axis. The spacer bodies are each adapted to be securely engaged with at least one of the control body and the user interface body for having a travel limiting portion thereof retained at a position between the force input portion of the control body and the user interface body.

In one or more embodiments of the disclosures made herein, a kit comprises a container, an imaging element cleaning apparatus and a plurality of spacer bodies. The container includes a first containment space and a second containment space. The imaging element cleaning apparatus is secured within the first containment space. The plurality of spacer bodies is secured within the second containment space. The imaging element cleaning apparatus includes a user interface body and a control body. The control body includes a force input (e.g., hand-gripping) portion and a mounting member having a first end portion thereof attached to the force input portion. A second end portion of the mounting member is movably attached to the user interface body to thereby enable axial displacement of the first end portion of the mounting member relative to the user interface body along an axial reference axis. Each of the spacer bodies has opposing surfaces thereof jointly defining a width thereof. Each of the spacer bodies is securely mountable on at least one of the control body and the user interface body whereby at least a portion of said opposing surfaces is positioned between the force input portion and the user interface body.

In one or more embodiments, a method for adapting an imaging element cleaning apparatus for use with a visualization scope comprises a plurality of steps. A step is provided for engaging the visualization scope with a chassis of the imaging element cleaning apparatus in a seated position. The imaging element cleaning apparatus includes a control body is translatably attached to the chassis for enabling movement of the control body between a fully retracted position and a fully displaced position relative to the chassis to thereby define an overall amount of axial displacement of the control body relative to the chassis along an axial reference axis. An imaging element surface of the visualization scope is axially spaced away from a cleaning member of the imaging element cleaning apparatus by an offset distance when the control body is in the fully displaced position. The cleaning member is fixedly coupled to the cleaning member whereby axial translation of the control body between the fully retracted position and the fully displaced position correspondingly causes axial translation of the cleaning member between a stowed position and a fully extended position. A step is provided for determining a particular spacer body of a set of spacer bodies having a spacer body width greater than the offset distance and less than the spacer body width of each other one of the spacer bodies of the set having a respective spacer body width greater than the offset distance. A step is proved for engaging the particular spacer body with at least one of the control body and the chassis to provide a spacer-limited amount of axial displacement of the control body relative to the user interface body.

It is an object of one or more embodiments of the disclosures made herein for the spacer body to include an engagement portion (e.g., the travel limiting portion) adapted for being manually clipped onto and detached from the mounting member.

It is an object of one or more embodiments of the disclosures made herein for the at least one spacer body to be clipped onto the mounting member.

It is an object of one or more embodiments of the disclosures made herein for the spacer body to include a handle portion attached to and extending from the engagement portion.

It is an object of one or more embodiments of the disclosures made herein for the handle portion of each of the spacer bodies to be identical to the handle portion of each other one of the spacer bodies.

It is an object of one or more embodiments of the disclosures made herein for the imaging element cleaning apparatus to further comprise an elongated body having a first end portion thereof attached to the user interface body and a cleaning member coupled to the control body for being located at a position axially spaced away from the second end portion of the elongated body.

It is an object of one or more embodiments of the disclosures made herein for the elongated body and user interface body to be jointly configured for having the visualization scope engaged therewith in a seated position with respect to the user interface body whereby an imaging element surface of the visualization scope is at a fixed location relative to a visualization scope seating surface of the user interface body.

It is an object of one or more embodiments of the disclosures made herein for a width of the at least one spacer body enables the cleaning member to be brought into contact with the imaging element surface of the visualization scope when the control body is fully displaced toward the user interface body.

It is an object of one or more embodiments of the disclosures made herein for a kit to further comprise a spacer body holder having a plurality of spacer body receiving spaces.

It is an object of one or more embodiments of the disclosures made herein for each of the spacer bodies to be disposed within a respective one of said spacer body receiving spaces.

It is an object of one or more embodiments of the disclosures made herein for each of the spacer bodies clipped onto a respective clipping member of the spacer body holder within a respective one of said spacer body receiving spaces thereof.

It is an object of one or more embodiments of the disclosures made herein for a width of each of the spacer body receiving spaces to be approximately the same as the width of the travel limiting portion (e.g., opposing surfaces) of the respective one of the spacer bodies disposed therein.

It is an object of one or more embodiments of the disclosures made herein for the spacer body holder to have indicia adjacent to each of the spacer body receiving spaces designating the width of the travel limiting portion of the respective one of the spacer bodies disposed therein.

It is an object of one or more embodiments of the disclosures made herein for a kit to further comprise a container having a cleaning apparatus receiving space and a plurality of spacer body receiving spaces integral therewith.

It is an object of one or more embodiments of the disclosures made herein for the imaging element cleaning apparatus is disposed within the cleaning apparatus receiving space of the container and for each of the spacer bodies is disposed within a respective one of said spacer body receiving spaces of the container.

It is an object of one or more embodiments of the disclosures made herein for a kit to further comprise a container including a first containment space and a second containment space, for the imaging element cleaning apparatus to be secured within the first containment space of the container and for the plurality of spacer bodies to be secured within the second containment space of the container.

It is an object of one or more embodiments of the disclosures made herein for the imaging element cleaning apparatus to be a sterile-packaged imaging element cleaning apparatus whereby the sterile-packaged imaging element cleaning apparatus is secured within the first containment space of the container and for the plurality of spacer bodies to be a sterile-packaged set of spacer bodies whereby the sterile-packaged set of spacer bodies is secured within the second containment space of the container.

It is an object of one or more embodiments of the disclosures made herein for the sterile-packaged set of spacer bodies to include a package having a spacer body holder integral therewith and for the spacer body holder to include a plurality of spacer body receiving spaces.

It is an object of one or more embodiments of the disclosures made herein for each spacer body of the set to include an engagement portion adapted for being manually clipped onto and detached from the control body and for engaging the particular spacer body with the control body to include clipping the particular spacer body onto the control body.

It is an object of one or more embodiments of the disclosures made herein for determining the particular spacer body to include inserting at least one of the spacer bodies of the set into a space between the cleaning member and the imaging element surface when the control body is in the fully displaced position.

It is an object of one or more embodiments of the disclosures made herein for determining the particular spacer body to include inserting at least one of the spacer bodies of the set into a space between the force input portion and the chassis when the cleaning member is in contact with the imaging element surface.

It is an object of one or more embodiments of the disclosures made herein for engaging the particular spacer body with the control body to include attaching the particular spacer body to at least one of the force input portion, the mounting member and the chassis.

It is an object of one or more embodiments of the disclosures made herein for each spacer body of the set to include an engagement portion adapted for being manually clipped onto and detached from the control body and for engaging the particular spacer body with the control body to include clipping the particular spacer body onto the mounting member.

These and other objects, embodiments, advantages and/or distinctions of the present invention will become readily apparent upon further review of the following specification, associated drawings and appended claims.

BRIEF DESCRIPTION OF THE DRAWINGS

FIG. 2 is a perspective view showing the imaging element cleaning apparatus and spacer body of FIG. 1, wherein the control body is in a travel-limited position as provided for by the spacer body causing a spacer-limited amount of axial displacement of the control body.

FIG. 3 is partial perspective view showing use and stowed positions of a cleaning member of the imaging element cleaning apparatus in relation to an imaging element of a prior art visualization scope seated thereon, wherein the use and stowed positions correspond respectively to the travel-limited position and extended position of the control body.

FIG. 4A is perspective view showing the spacer body of FIG. 1.

FIG. 4B is side view showing the spacer body of FIG. 1.

DETAILED DESCRIPTION

Figure 1A:
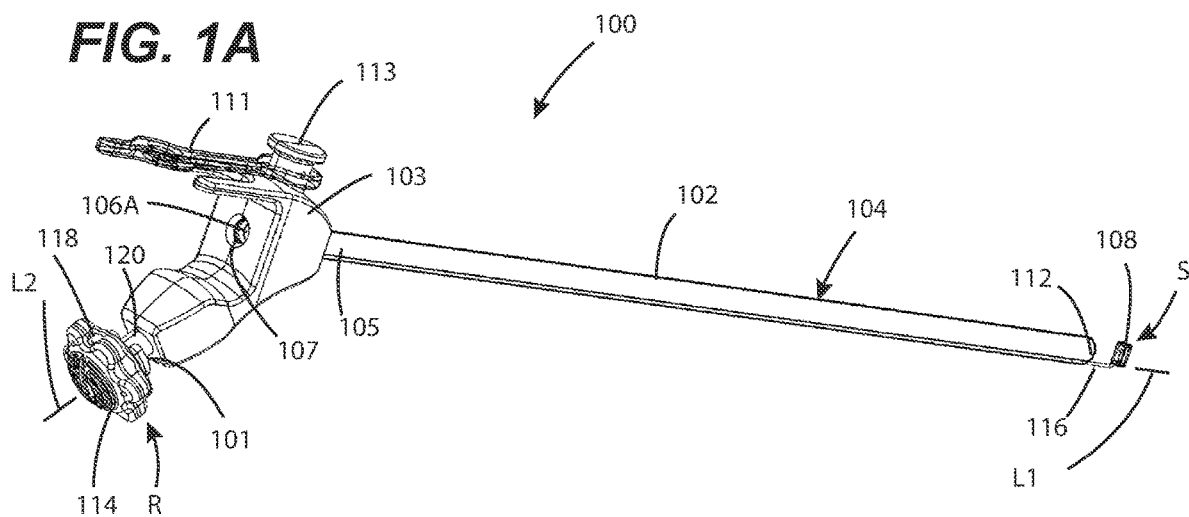
FIG. 1A is a perspective view showing a prior art imaging element cleaning apparatus having mounted thereon a spacer body configured in accordance with one or more embodiment of the disclosures made herein, wherein a control body of the imaging element cleaning apparatus is in an extended position thereof.
Figure 1B:
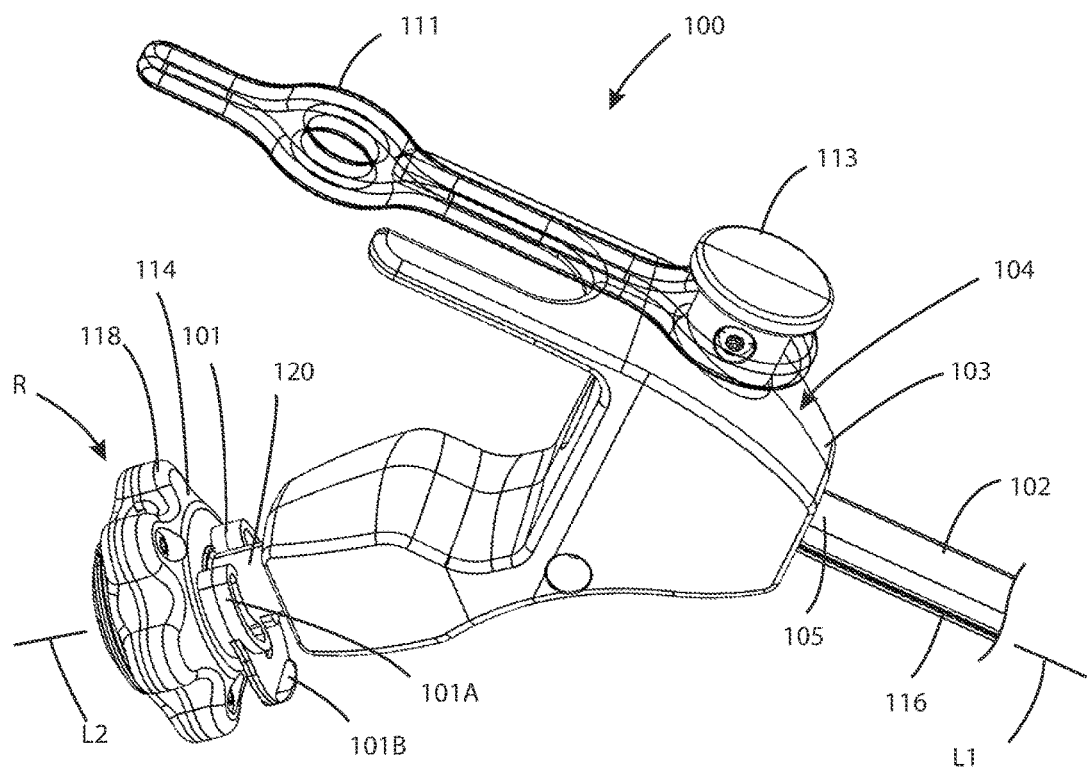
FIG. 1B is an enlarged partial perspective view showing a user interface portion of the imaging element cleaning apparatus and spacer body of FIG. 1.

FIGS. 1-3 illustrate various aspects of an imaging element cleaning apparatus configured in accordance with one or more embodiments of the disclosures made herein, which is designated as cleaning apparatus 100. The cleaning apparatus 100 is preferably, but not necessarily, configured to be used with commercially-available visualization scopes such as, for example, an endoscope, laparoscope and the like. In some embodiments, the cleaning apparatus 100 is preferably, but not necessarily, configured to be used with one or more visualization scopes each manufactured under brand name(s) of Karl Storz, Linvatec, Olympus, Richard Wolf, Stryker and Intuitive Surgical. Thus, in preferred embodiments, cleaning apparatus 100 can be engineered as endoscope-specific for a given model(s) of one or more manufacturers based on the dimensional attributes of such commercially-available visualization scopes. An underlying consideration of the manner in which the cleaning apparatus 100 is engineered for an intended brand(s) or model(s) of endoscope is that there be a high level of dimensional precision between the endoscope and the cleaning apparatus 100. Such dimensional precision can be characterized to include both the inhibition of any unacceptable level of relative movement between the visualization scope and the cleaning apparatus 100 and the relative placement of key structural elements of the endoscope relative to those of the cleaning apparatus 100.

The cleaning apparatus 100 is an example of an operative apparatus configured in accordance with the disclosures made herein. To this end, through use of a spacer body 101 (or plurality thereof), the cleaning apparatus 100 is adapted for mitigating adverse implications of adjusting a control portion of the operative apparatus to a user-defined setting that is not a predefined setting position of the operative apparatus. Such adverse implications generally arise due to the time required for performing such adjustment with a required degree of precision. In this manner, the cleaning apparatus 100 serves to mitigate, if not eliminate, that manner in which adjusting the control portion of the operative apparatus to the user-defined setting during a procedure (e.g., a surgical procedure) can undesirably and/or unacceptably limit efficiency and/or effectiveness of the procedure.

Still referring to FIGS. 1-3, the cleaning apparatus 100 includes the spacer body 101, an elongated body 102 and a user interface body 103, which jointly define a chassis 104. The elongated body 102 is attached at a proximate end portion 105 thereof to the user interface body 103. The elongated body 102 and the user interface body 103 (i.e., the chassis 104) serves as a platform on which a visualization scope may be mounted in a predictable seated position. In one or more embodiments, the user interface body 103 or the chassis 104 may be a main body of the cleaning apparatus 100. The elongated body 102 may be a tube having a central passage 106 with a round or generally round cross-sectional shape. The central passage 106 may be accessible through a mating opening 106A (or other form of passage) within the user interface body 103 thereby enabling the extension portion (e.g., imaging element carrying wand) of the visualization scope to be inserted into the central passage 106 through the opening 106A.

The central passage 106 has a size and profile that is adapted to have the extension portion of the visualization scope engaged therein by inserting the extension portion through the opening 106A of the user interface body 103 and sliding the extension portion along the length of the elongated body 102 until the visualization scope is in the seated position S on the chassis 104. Alternatively, the elongated member 102 may be a non-tubular structure such as a skeletal-type structure that engages the extension portion of the visualization scope—e.g., at discrete spaced-apart locations thereof.

In preferred embodiments, the chassis 104 may include a plurality of structural elements that provide for the known and predictable position of the visualization scope when mounted in the seated position on the chassis 104. One of these structural elements is the effective inside diameter (e.g., for ribbed or textured interior surface) or the actual inside diameter (e.g., a smooth interior wall) of the elongated body 102 in relation to an outside diameter of the extension portion of the visualization scope. It is preferable to maintain a close fit between the wall of elongated body 102 and the mating exterior surface of the extension portion 1 of the visualization scope so as to provide for a fluid-resistant interface between the elongated body 102 and the extension portion and to limit off-axis pitch between a longitudinal axis of the elongated body 102 and a longitudinal axis of the extension portion. When the visualization scope is fully compatible with the cleaning apparatus 100, another one of these structural elements is a seating surface 107 (shown in FIG. 1A) on the user interface body 103. The seating surface 107 may be a reference surface of the cleaning apparatus 100 that engages a mating reference surface of the visualization scope (e.g., a machined surface thereof) for defining a seated position of the visualization scope on the chassis 104. Thus, engagement of the seating surface 107 with the mating reference surface of the visualization scope serves to define a predictable seated position of the visualization scope relative to various components of the cleaning apparatus 100.

The cleaning apparatus 100 include a cleaning member 108 adjacent to an opening 110 in a distal end portion 112 of the elongated body 102. The opening 110 is defined by the central passage 106 of the elongated body 102. As shown in FIG. 3, the cleaning member 108 functions to engage an imaging element surface 1A (e.g., a lens, optical window or the like) of an endoscope 1 to clean contaminants and debris therefrom when the cleaning member 108 is brought into contact with (e.g., wiped across) the imaging element surface 1A. The cleaning member 108 may be any type of suitable element for cleaning contaminants and debris from the imaging element surface 1A of an endoscope 1—e.g., a wiping element such as a resilient/polymeric wiper, an absorbent element such as a sponge or the like.

For facilitating the cleaning member 108 being brought into contact with the imaging element surface 1A, the cleaning apparatus 100 includes a control body 114 (e.g., a control knob) that is fixedly coupled to the cleaning member 108 through a coupling element 116. For example, a first end portion of the coupling element 116 may be fixedly attached to the cleaning member 108 and a second end portion of the coupling element 116 may be fixedly attached to the control body 114. Such fixed attachment preferably inhibits unrestricted rotational movement of coupling element relative to the cleaning member 108 and the control body 114. The coupling element 116 is coupled to the elongated body 102 for enabling rotational translation (i.e., rotational movement) about a first axial reference axis L1 and is translatably coupled (i.e., axially) to the elongated body 102 for enabling axial translation (i.e., axial movement) along the first axial reference axis L1. For example, the coupling element 116 may be disposed within elongated passage (e.g., a channel, groove or the like) of the elongated body 102 that extends approximately parallel to the central passage 106 of the elongated body 102 for permitting rotational and axial translation of the coupling element 116 relative to the elongated body 102.

In some embodiments, the coupling element 116 may be an elongated small diameter structure that offers at least a limited degree of bendability in combination with high torsional rigidity. In other embodiments, the coupling element 116 is characterized by an elongated small diameter structure that offers a given amount of torsional compliance. Based on these characterizing attributes, examples of coupling element 116 include, but are not limited to, solid metallic wire, spiraled metal wire, a polymeric filament(s), a composite filament(s) or the like.

The control body 114 includes a hand-gripping portion 118 and a mounting member 120. A first end portion of the mounting member 120 is attached to the hand-gripping portion 118. A second end portion of the mounting member 120 is movably attached to the user interface body 103 for enabling rotational movement and axial translational movement of the control body 114 with respect to the user interface body 103. As shown in FIG. 3, in view of the control body 114 being fixedly coupled to the cleaning member 108 through the coupling element 116, axial displacement (i.e., movement) of the control body 114 results in a corresponding axial displacement of the cleaning member 108 relative to the distal end portion 112 of the elongated body along an axial reference axis L1 and rotational displacement (i.e., rotational movement) of the control body 114 results in a corresponding rotational displacement of the cleaning member 108 relative to the distal end portion 112 of the elongated body 102 about the axial reference axis L1. Thus, through axial and rotational displacement of the control body 114 via manual force application to the hand-gripping portion 118 thereof, the cleaning member 108 may be selectively moved axially along the axial reference axis L1 between a stowed position S and a use position U with respect to the distal end portion 112 of the elongated body 102 and may be selectively rotated about the axial reference axis L1 for enabling the cleaning member 108 to be moved into and away from contact with the imaging element surface 1A of the visualization scope 1 while the cleaning member is in the use position U.

The hand-gripping portion 118 of the control body 114 is an example of a force input portion. A force input portion of a control body that is intended to be gripped by a hand is most applicable to manually-operated imaging element cleaning apparatuses. However, in some embodiments, the imaging element cleaning apparatuses may be operated by a system or machine such as, for example, a robotic surgical system. In such embodiments, a force input portion of a control body may be engaged by an actuator of the system or machine for applying rotational and axial translation forces thereto.

To provide for securement between and/or rotational clocking of the visualization scope 1 and the cleaning apparatus 100, the user interface body 103 may include a light port receptacle 111 and one or more securement bodies 113. The light port receptacle 111 has a light port receiving space 115 in which a light port of the visualization scope 1 is received (e.g., constrained by engagement of mating surfaces) while the visualization scope 1 is engaged with the cleaning apparatus 100. A retention structure 115 (e.g., an elastic strap, band of the like) may be engaged with the one or more securement bodies 113 to secure the visualization scope 1 and the cleaning apparatus 100 in fixed, seated engagement.

Discussed now in greater detail is the manner in which the spacer body 101 (or plurality thereof) advantageously mitigate adverse implications previously associated with adjusting a control portion (e.g., the control body 114) of an operative apparatus (e.g., cleaning apparatus 100) to a user-defined setting that is not a predefined setting position of the operative apparatus. Specifically, as shown in FIGS. 1-3, an engagement portion 101A of the spacer body 101 (or plurality thereof) may be configured for enabling the spacer body 101 to be detachably clipped onto (i.e., attached to/mounted on) the mounting member 120 of the control body 114—e.g., a clip member of the spacer body 101. Alternatively or additionally, the spacer body 101 (or plurality thereof) may be configured to be attached to the hand-gripping portion 118 of the control body 114 and/or to a portion of the user interface body 103 adjacent to the mounting member 120 (e.g., a wall thereof through which the mounting member 120 extends). The spacer body 101 may have a handle portion 101B attached to and extending from the engagement portion 101 of the spacer body 101, thereby facilitating attachment of the spacer body 101 to the required structure of the cleaning apparatus 100.

The spacer body 101 is used to reduce axial displacement of the control body 114 from an overall amount of axial displacement without installation of the spacer body 101 (or plurality thereof) to a spacer-limited amount of axial displacement thereof with installation of the spacer body 101 (or plurality thereof). The overall amount of axial displacement corresponds to travel of the control body 114 between a fully retracted position R (see FIGS. 1A and 1B) where the hand-gripping portion 118 is retracted fully away from the user interface body 103 and a fully displaced position where the hand-gripping portion 118 is displaced fully toward the user interface body 103. The spacer-limited amount of axial displacement thereof corresponds to travel of the control body 114 between the fully retracted position R and a limited-travel position L (see FIG. 2) where the hand-gripping portion 118 is displaced toward the user interface body 103 by an amount limited by width W of the spacer body 101 (or plurality thereof). Correspondingly, the cleaning member 108 is in the stowed position S when the control body 114 is in the fully retracted position R and is in a fully extended position when the control body is in the fully displaced position.

The spacer body 101 reduces the overall amount of axial displacement of the control body 114 by an amount equal to (or approximately equal to) a width W of the spacer body 101 (or plurality thereof). The width W of the spacer body 101 is defined by opposing surfaces S1, S2 of the engagement portion 101A (e.g., a travel limiting portion) of spacer body 101. Such reduction in the overall amount of axial displacement of the control body 114 is adjusted through the use of one or more spacer bodies (e.g., the spacer body 101) to achieve the spacer-limited amount of axial displacement. Thus, translation of the control body 114 from the fully retracted position R (see FIGS. 1A and 1B) to a limited-travel position L results in the cleaning member 108 correspondingly moving from the stowed position S to the use position U (see FIG. 3) as provided for by the spacer-limited amount of axial displacement of the control body 114.

Without use of the spacer body 110 (or plurality thereof), the overall amount of axial displacement of the control body 114 would result in the cleaning member 108 being at an unacceptable position when the control body 114 is axially translated toward to the user interface body 103 by the entire overall amount of axial displacement—e.g., the cleaning member 108 being too far forward to the imaging element surface 1A of the visualization scope 1. Accordingly, without use of the spacer body 101 (or plurality thereof), a user of the cleaning apparatus 100 would need to manually seek to find a location of the control body 114 that suitably positions the cleaning member 108 (see FIG. 3) for cleaning of the imaging element surface 1A of the visualization scope 1 when the control body 114 is rotationally translated for bringing the cleaning member 108 into and away from contact with the imaging element surface 1A. Such need to manually seek to find the location of the control body 114 that suitably positions the cleaning member 108 for cleaning of the imaging element surface 1A arises due to variations in location of the imaging element surface 1A relative to a reference position of the cleaning apparatus 100—e.g., the seating surface 107 of cleaning apparatus 100 relative to the mating structure of the visualization scope 1.

A person of ordinary skill in the art will understand that variations in location of an imaging element surface may be due to extending utility of a single imaging element cleaning apparatus across a plurality of different models, brands and/or sizes of visualization scopes, to dimensional variations in a given model of visualization scope, to dimensional variations in the model of imaging element cleaning apparatus and/or the like. A person of ordinary skill in the art will also understand that these types of variations generally preclude a single (e.g., overall) amount of axial displacement of the control body from accommodating cleaning member positioning requirements of multiple visualization scopes with a particular imaging element cleaning apparatus or a plurality of different imaging element cleaning apparatuses. It is well known that different brands and models of visualization scopes often have one or more other dimensional considerations (e.g., extension member length, seating surface size/shape, light port placement, etc.) that influence placement of the imaging element surface of a particular visualization scope with respect to the cleaning member of a given imaging element cleaning apparatus with which the particular visualization scope is engaged. Hence the need for a user of a conventionally configured imaging element cleaning apparatus (i.e., without one or more spacer bodies installed) to manually seek to find a location of the control body that suitably positions the cleaning member for cleaning of the imaging element surface of the visualization scope. Advantageously, spacer bodies in accordance with the disclosures made herein overcome such need for a user of a conventionally configured imaging element cleaning apparatus to manually seek to find a location of the control body that suitably positions the cleaning member for enabling acceptable cleaning of the imaging element surface of the visualization scope.

Accordingly, in accordance with embodiment of the disclosures made herein, a spacer body of a given width or a plurality of spacer bodies of a common and/or different widths is used to provide the aforementioned spacer-limited amount of axial displacement for a particular device (e.g., visualization scope) to be used with a particular operative apparatus (e.g., imaging element cleaning apparatus), for a prescribed brand/model of device to be used with a designated configuration/construction of operative apparatus and the like. In this manner, operative apparatuses configured in accordance with embodiment of the disclosures made herein (e.g., imaging element cleaning apparatuses) serves to mitigate, if not eliminate, the manner in which adjusting a control body thereof for achieving a user-defined setting that is not a predefined setting position of the operative apparatus advantageously enhances efficiency and effectiveness of the operative apparatus and a procedure in which the operative apparatus is used.

Various methods may be implemented for using spacer bodies in accordance with the disclosures made herein achieve desired operative (e.g., imaging element surface cleaning) functionality by reduce axial displacement of a control body of an operative apparatus from an overall amount of axial displacement to a spacer-limited amount of axial displacement thereof. In one such implementation, a spacer body width (i.e., as provided for by one or more spacer bodies) required for achieving a necessary spacer-limited amount of axial displacement is determined based upon known dimensional values of an operative apparatus and an associated device to be utilized with the operative apparatus. For example, based upon such known dimensional values of the operative apparatus and the associated device, the required spacer body width may be numerically computed. Such computation may be based on dimensional information correlating to an amount of contact between a particular structural component (e.g., cleaning member) of the operative apparatus and a corresponding structural component (e.g., imaging element surface) of the associated device, on an amount of deflection and/or applied force of the structural component of the operative apparatus when in contact with associated structural component of the associated device, an efficiency of operation (e.g., amount of reference contaminant removed from an imaging element surface) or the like. In another such implementation, a spacer body width (i.e., as provided for by one or more spacer bodies) required for achieving a necessary spacer-limited amount of axial displacement is determined based upon trial-and-error fitment of spacer bodies on mating portion of an operative apparatus (e.g., a control body of an imaging element cleaning apparatus). For example, after engaging an imaging element cleaning apparatus with a visualization scope, different width spacer bodies (i.e., individually and/or in combination) are attached to a control body of the imaging element cleaning apparatus and a required spacer body width is assessed—e.g., by empirically or experimentally determining an amount of contact between the cleaning member and imaging element surface, an amount of deflection and/or applied force of the cleaning member when in contact with the imaging element surface, an amount of reference contaminant removed from the imaging element surface or the like.

As disclosed herein, an imaging element cleaning apparatus may be adapted for use with a visualization scope. One or more spacer bodies or other similar structural body may be used to facilitated adapting the imaging element cleaning apparatus for use with a visualization scope. As previously discussed, through such adaption, adverse implications of adjusting a control portion of the operative apparatus to a user-defined setting that is not a predefined setting position of the operative apparatus are mitigated, if not eliminated.

In one or more embodiments of the disclosure made herein, a method of adapting the imaging element cleaning apparatus for use with a visualization scope comprises begins with engaging the visualization scope (e.g., visualization scope 1 in FIG. 3) with a chassis (e.g., chassis 104 shown in FIGS. 1A, 1B and 2) of the imaging element cleaning apparatus (e.g., cleaning apparatus 100 shown in FIGS. 1A, 1B and 2) in a seated position—i.e., a known fixed predictable position of the visualization scope relative to the imaging element cleaning apparatus. For example, an extension portion of the visualization scope can be inserted into an elongated body (e.g., elongated body 102 shown in FIGS. 1A, 1B, 2 and 3) of the imaging element cleaning apparatus. The imaging element cleaning apparatus includes a control body (e.g., control body 114 shown in FIGS. 1A, 1B and 2) that is translatably attached to the chassis for enabling movement of the control body between a fully retracted position (e.g., fully retraced position R shown in FIGS. 1A and 1B) and a fully displaced position (i.e., discussed above) relative to the chassis to thereby define an overall amount of axial displacement of the control body relative to the chassis along an axial reference axis (e.g., axial reference axis L1). With the visualization scope in the seated position relative to the imaging element cleaning apparatus, an imaging element surface of the visualization scope (e.g., imaging element surface 1A shown in FIG. 3) is axially spaced away from a cleaning member of the imaging element cleaning apparatus (e.g., cleaning member 108 shown in FIGS. 1A, 1B, 2 and 3) by an offset distance when the control body is in the fully displaced position. The cleaning member is fixedly coupled to the cleaning member whereby axial translation of the control body between the fully retracted position and the fully displaced position correspondingly causes axial translation of the cleaning member between a stowed position (e.g., stowed position S shown in FIGS. 1A and 3) and a fully extended position (i.e., discussed above).

Next, a particular spacer body of a set of spacer bodies (e.g., spacer body 101 shown in FIGS. 1A, 1B and 2) having a spacer body width greater than the offset distance and less than the spacer body width of each other one of the spacer bodies of the set having a respective spacer body width greater than the offset distance is determined. Determining the particular spacer body may include inserting at least one of the spacer bodies of the set into a space between the cleaning member and the imaging element surface when the control body is in the fully displaced position. Determining the particular spacer body may include inserting at least one of the spacer bodies of the set into a space between the force input portion and the chassis when the cleaning member is in contact with the imaging element surface.

Thereafter, the particular spacer body is engaged with at least one of the control body and the chassis to provide a spacer-limited amount of axial displacement of the control body relative to the user interface body. Engaging the particular spacer body with the control body may include attaching the particular spacer body to at least one of a force input portion of the control body (e.g., force input portion 118 shown in FIGS. 1A, 1B and 2), a mounting member of the control body (e.g., mounting member 120 shown in FIGS. 1A and 1B) and the chassis (e.g., the user interface portion 103 shown in FIGS. 1A, 1B and 2). Each spacer body of the set may an engagement portion (e.g., engagement portion 101A shown in FIGS. 4A and 4B) adapted for being manually clipped onto and detached from the control body and/or chassis and engaging the particular spacer body with the control body and/or chassis may include clipping the particular spacer body onto the control body and/or the chassis.

Figure 5:
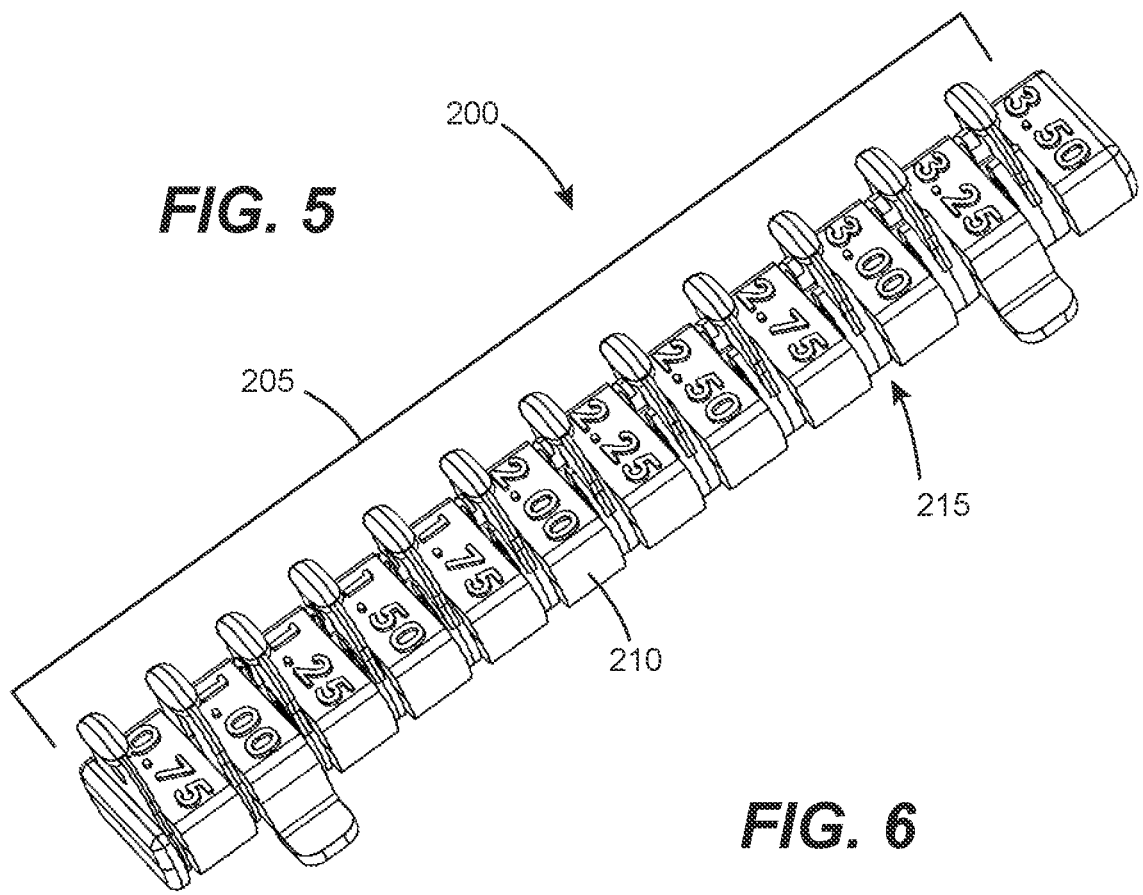
FIG. 5 is a perspective view showing a set of spacer bodies configured in accordance with one or more embodiment of the disclosures made herein.
Figure 6:
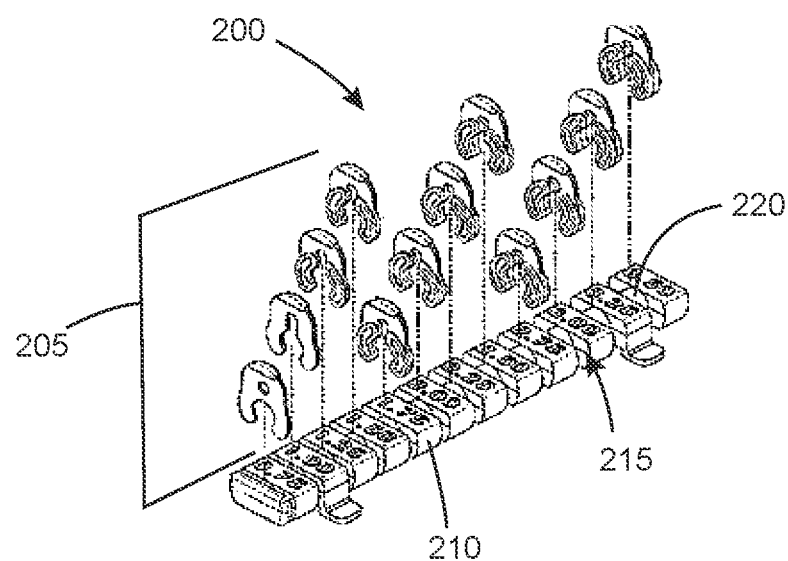
FIG. 6 is exploded perspective view of the set of spacer bodies shown in FIG. 5.

Referring now to FIGS. 5 and 6, a spacer body unit 200 including a set of spacer bodies 205 and a spacer body holder 210 is shown. Each spacer body of the set 205 are configured for being mounted on an operative apparatus (e.g., an imaging element cleaning apparatus) to reduce axial displacement of a control body of the operative apparatus from an overall amount of axial displacement to a spacer-limited amount of axial displacement. To this end, each spacer body of the set 205 may be configured in a manner identical to or functionally equivalent to the spacer body 101 discussed above in reference to FIGS. 1-4—e.g., including an engagement portion configured for enabling the spacer body to be detachably clipped onto a mating portion (e.g., control body and/or user interface body) of an operative apparatus.

The spacer body holder 210 has a plurality of spacer body receiving spaces 215. Each of the spacer bodies of the set 205 is disposed within a respective one of the spacer body receiving spaces 215. In one or more embodiments, each of the spacer bodies of the set 205 may be clipped (or otherwise detachably engaged with) a respective attachment (e.g., clipping) member 220 of the spacer body holder 215 within a respective one of the spacer body receiving spaces 215. A width of each of the spacer body receiving spaces 215 may be approximately the same as the width of the respective one of the spacer bodies of the set 200 disposed therein. The spacer body holder 210 may include indicia adjacent to each of the spacer body receiving spaces 215 designating the width of the respective one of the spacer bodies of the set 200 disposed therein. The spacer bodies of the set 200 may range from a minimum width to a maximum width anticipated for achieving a required/desired spacer-limited amount of axial displacement for a particular operative apparatus (e.g., an imaging element cleaning apparatus) and associated device (e.g., a visualization scope) or collection of associated devices.

Embodiments of the disclosures made herein may include kits comprising an operative apparatus (e.g., an imaging element cleaning apparatus configured in a manner identical to or functionally equivalent to the imaging element cleaning apparatus 100 discussed above in reference to FIGS. 1-3) and a set of spacer bodies (e.g., configured in a manner identical to or functionally equivalent to the spacer body 101 discussed above in reference to FIGS. 1-4). Such kits may be used, for example, by surgical personnel to configure the operative device of the kit to exhibit a desired/required spacer-limited amount of axial displacement for the operative apparatus of the kit and an associated device of collection of associated devices intended for use with the operative apparatus of the kit. For example, a surgical assistant or surgeon may use one or more spacer bodies of the kit to configure an imaging element cleaning apparatus of the kit to exhibit desired imaging element cleaning performance for a particular visualization scope to be used by a surgeon in a surgical procedure.

Figure 7:
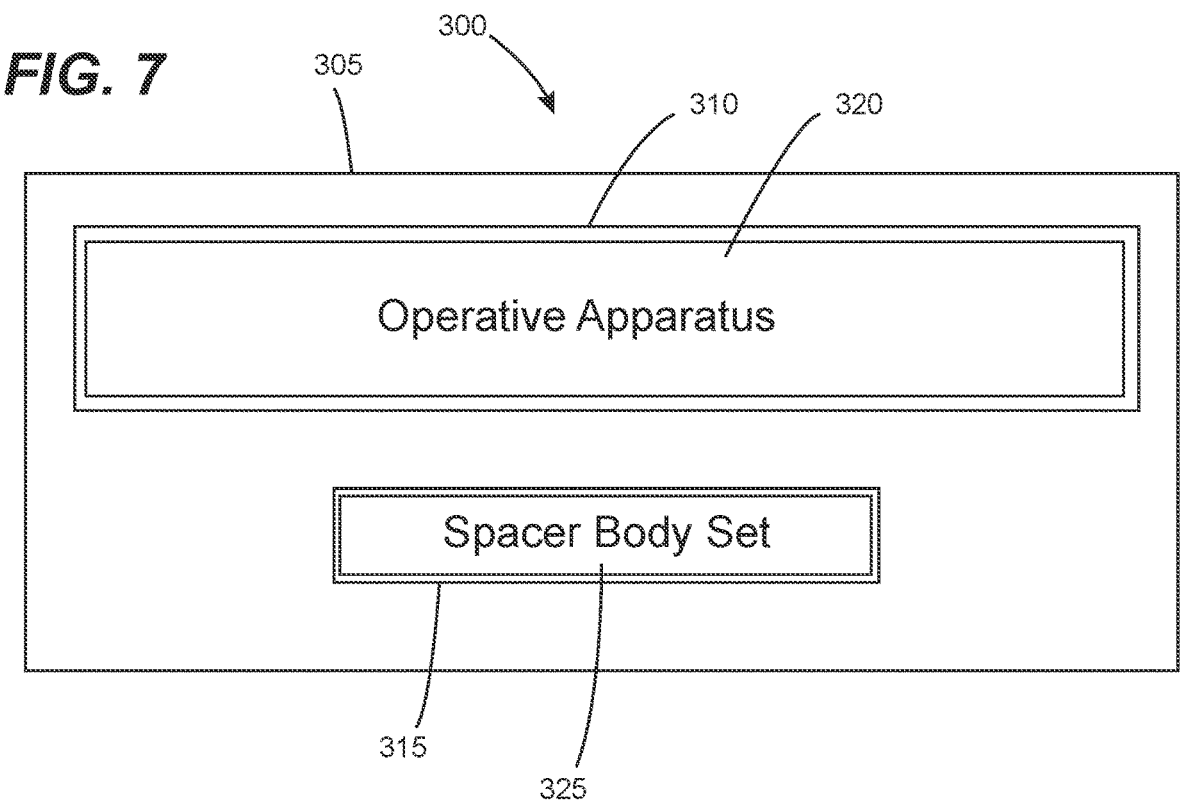
FIG. 7 is a diagrammatic view showing an operative apparatus kit configured in accordance with a first embodiment of the disclosures made herein.

FIG. 7 shows an operative apparatus kit 300 including a container 305 having a first containment space 310 and a second containment space 315. An operative apparatus 320 (e.g., an imaging element cleaning apparatus) is secured within the first containment space 310 and a set of spacer bodies 325 is secured within the second containment space 315. Securement of the operative apparatus 320 and the set of spacer bodies 325 may be provided for by any suitable means—e.g., mechanical securement, adhesive securement, film covering securement, clamshell securement, hermetic packaging securement or the like used for sterile packaging.

The operative apparatus 320 may be a sterile-packaged operative apparatus, whereby the sterile-packaged operative apparatus is secured within the first containment space 310. The set of spacer bodies 325 may be a sterile-packaged set of spacer bodies, whereby the sterile-packaged set of spacer bodies is secured within the second containment space 315. In this manner, the operative apparatus 320 and the set of spacer bodies 325 are each sealed in a sterile manner within a respective package and such respective packages are themselves secured within the respective containment space 310, 315 of the container 305. Advantageously, such a sterile packaged format of the operative apparatus 320 and the set of spacer bodies 325 enables the sterile-packaged operative apparatus 320 and the sterile-packaged set of spacer bodies 325 to be separately manufactured (e.g., at different manufacturing facilities) and subsequently integrated into kit form after being manufactured.

The spacer bodies of the set 325 may be in a form identical to or functionally similar to the spacer body unit 200 discussed above in reference to FIGS. 5 and 6. The spacer bodies of the set 325 may be engaged with a spacer body holder in a form identical to or functionally similar to the spacer body holder 210 discussed above in reference to FIGS. 5 and 6. The second containment space 315 may have a plurality of spacer body receiving spaces, where each spacer body receiving spaces is configured (e.g., sized and/or shaped) for having a respective one of the spacer bodies of the set 325 disposed therein.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. A method for adapting an imaging element cleaning apparatus for use with a visualization scope, comprising:
    engaging the visualization scope with a chassis of the imaging element cleaning apparatus in a seated position, wherein the imaging element cleaning apparatus includes a control body translatably attached to the chassis for enabling movement of the control body between a fully retracted position and a fully displaced position relative to the chassis to thereby define an overall amount of axial displacement of the control body relative to the chassis along an axial reference axis, wherein an imaging element surface of the visualization scope is axially spaced away from a cleaning member of the imaging element cleaning apparatus by an offset distance when the control body is in the fully displaced position, wherein the cleaning member is fixedly coupled to the control body whereby axial translation of the control body between the fully retracted position and the fully displaced position correspondingly causes axial translation of the cleaning member between a stowed position and a fully extended position;
    determining a particular spacer body of a set of spacer bodies having a spacer body width greater than the offset distance and less than the spacer body width of each other one of the spacer bodies of the set having a respective spacer body width greater than the offset distance; and
    engaging the particular spacer body with at least one of the control body and the chassis to provide a spacer-limited amount of axial displacement of the control body relative to the chassis.

2. The method of claim 1 wherein:
    each spacer body of the set includes an engagement portion adapted for being manually clipped onto and detached from the control body; and
    engaging the particular spacer body with the control body includes clipping the particular spacer body onto the control body.

3. The method of claim 1 wherein determining the particular spacer body includes inserting at least one of the spacer bodies of the set into a space between the cleaning member and the imaging element surface when the control body is in the fully displaced position.

4. The method of claim 1 wherein:
    the control body includes a force input portion and a mounting member having a first end portion thereof attached to the force input portion,
    a second end portion of the mounting member is movably attached to the chassis to thereby enable axial displacement of the first end portion of the mounting member relative to the chassis along the axial reference axis; and
    determining the particular spacer body includes inserting at least one of the spacer bodies of the set into a space between the force input portion and the chassis when the cleaning member is in contact with the imaging element surface.

5. The method of claim 4 wherein engaging the particular spacer body with the control body includes attaching the particular spacer body to at least one of the force input portion, the mounting member and the chassis.

6. The method of claim 1 wherein:
- the control body includes a force input portion and a mounting member having a first end portion thereof attached to the force input portion,
- a second end portion of the mounting member is movably attached to the chassis to thereby enable axial displacement of the first end portion of the mounting member relative to the chassis along the axial reference axis; and
- engaging the particular spacer body with the control body includes attaching the particular spacer body to at least one of the force input portion, the mounting member and the chassis.

7. The method of claim 6 wherein:
- each spacer body of the set includes an engagement portion adapted for being manually clipped onto and detached from the control body; and
- engaging the particular spacer body with the control body includes clipping the particular spacer body onto the mounting member.

* * * * *